US005600024A

United States Patent [19]

Eldridge et al.

[11] Patent Number: 5,600,024

[45] Date of Patent: Feb. 4, 1997

[54] ENHANCED RECOVERY OF ALCOHOL FROM AN ETHER CONTAINING STREAM

[75] Inventors: Robert B. Eldridge; Gary R. Patton, both of Bartlesville, Okla.

[73] Assignee: Phillips Petroleum Company, Bartlesville, Okla.

[21] Appl. No.: 507,578

[22] Filed: Jul. 26, 1995

[51] Int. Cl.[6] ............................ C07C 41/06; C07C 41/09

[52] U.S. Cl. .......................... 568/697; 568/694; 568/696; 568/698

[58] Field of Search .................................... 568/694, 696, 568/697, 698

[56] References Cited

U.S. PATENT DOCUMENTS

| | | | |
|---|---|---|---|
| 4,306,407 | 6/1982 | Smith, Jr. et al. | 568/697 |
| 5,237,115 | 8/1993 | Makovec et al. | 585/314 |
| 5,248,836 | 9/1993 | Bakai et al. | 568/697 |
| 5,318,689 | 6/1994 | Hsing et al. | 208/70 |

*Primary Examiner*—Gary Geist
*Assistant Examiner*—Dwayne C. Jones
*Attorney, Agent, or Firm*—Charles W. Stewart

[57] ABSTRACT

A process for producing ethyl tertiary butyl ether and for the substantially complete recovery by fractional distillation of the unreacted ethanol contained in an etherification reaction zone product stream as a product along with the ethyl tertiary butyl ether reaction product. This process utilizes methanol as a fractionator feed additive to enhance the recovery of ethanol as a bottoms product.

16 Claims, 2 Drawing Sheets

10
34
16
20
38
18
36
40
32
14
30
28
26
24
12b
42
12a
22

ENHANCED RECOVERY OF ALCOHOL FROM AN ETHER CONTAINING STREAM

This invention relates to the enhanced recovery of alcohol contained in an etherification reactor effluent stream.

Ether compounds are well known as blending components for gasoline. In certain etherification processes, ether compounds are produced by reacting an isoolefin with an alcohol within a reaction zone. The reaction product from the etherification reaction zone undergoes a separation to remove the ether product from the non-reactive and unreacted components of the etherification reaction zone feed. In the case of ethyl tertiary butyl ether (ETBE) production, the azeotropes that form between ethanol and hydrocarbon make the substantial recovery of ethanol, along with the ETBE bottoms product from the etherification reaction product fractionator, difficult. Furthermore, when a mixed butene stream is used as an etherification reaction zone feed, the non-reactive hydrocarbons are charged along with the resultant reaction product to the etherification reaction product fractionator and pass with its overhead stream to downstream processing. The presence of ethanol in the non-reactive hydrocarbons often are undesirable contaminants to the downstream units that process such non-reactive hydrocarbons.

It is an object of this invention to provide for an enhanced removal and recovery of the ethanol contained in an etherification reaction zone product stream.

It is a further object of this invention to provide for a substantial reduction in the amount of ethanol that passes with the overhead product of an etherification reaction zone product fractionator.

A still further object of this invention is to provide for the substantial recovery of ethanol from an etherification reaction zone product stream as a part of the bottoms product of the etherification reaction zone product fractionator.

One embodiment of the invention is a method for improving the recovery of ethanol contained in an etherification zone reaction product stream containing ethyl tertiary butyl ether, ethanol and hydrocarbons. To enhance the recovery of ethanol from the etherification zone reaction product stream, a concentration of methanol is provided in the etherification zone reaction product stream such that the molar ratio of methanol to ethanol is in the range of from about 0.1:1 to about 10:1. The etherification reaction zone product stream is thereafter separated by fractional distillation into an overhead stream, containing methanol and hydrocarbons, and a bottoms stream, containing ETBE and ethanol.

Another embodiment of the invention is a method for producing ETBE by reacting a stream containing isobutylene, ethanol and non-reactive hydrocarbons within an etherification reaction zone to form a reaction product containing ETBE, unreacted ethanol and non-reactive hydrocarbons. Methanol is added to the reaction product in such an amount as to give a fractionator feed having a molar ratio of methanol to ethanol in the range of from about 0.1:1 to about 10:1. The fractionator feed is separated by fractional distillation into an overhead stream and a bottoms stream. The overhead stream contains methanol and non-reactive hydrocarbons and the bottoms stream contains ETBE and ethanol.

Figure 1:
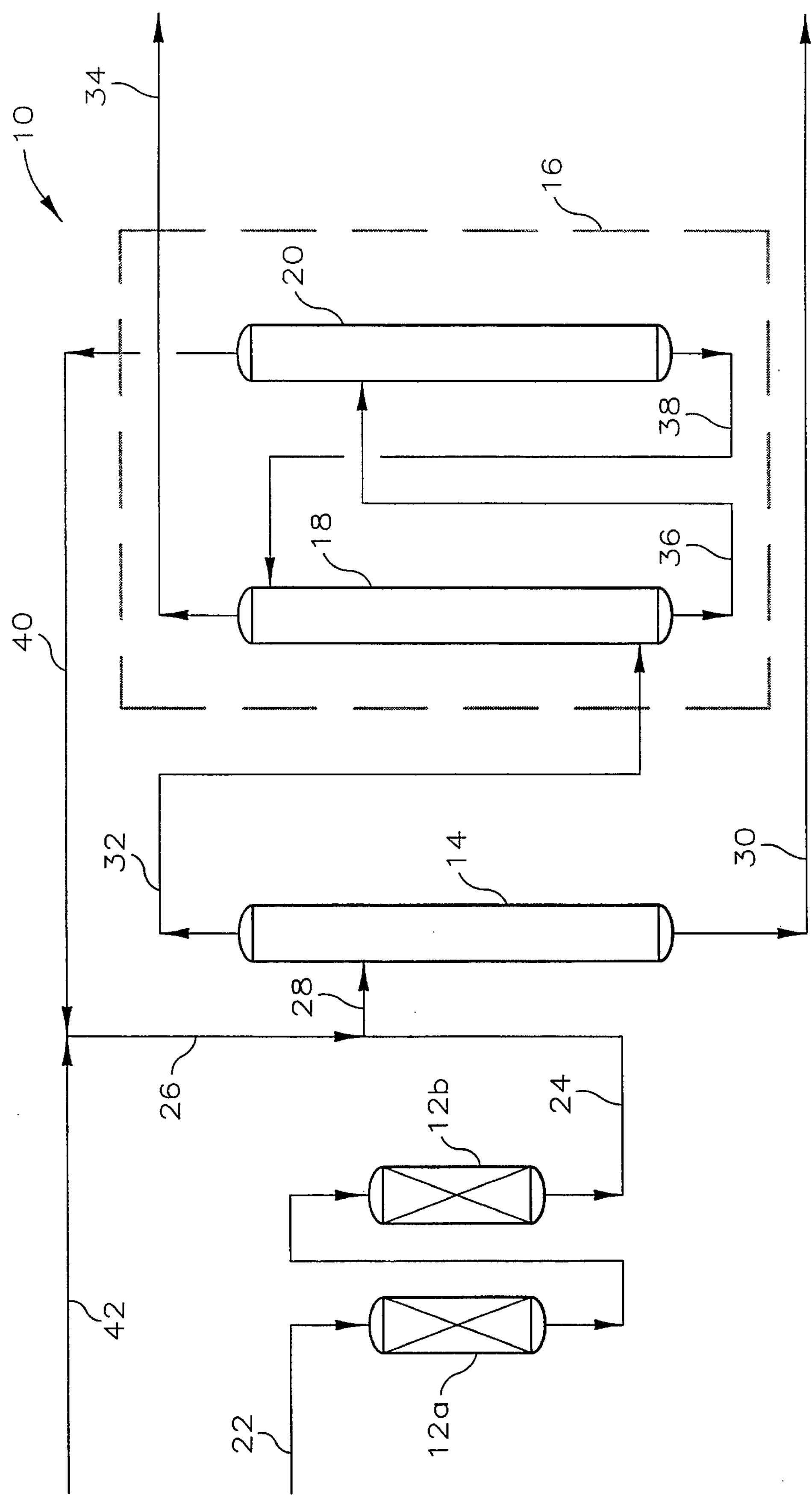
FIG. 1 is a schematic representation of a process which is one embodiment of the invention.

Other objects and advantages of the invention will be apparent from the following detailed description of the invention and the appended claims.

The inventive process solves certain of the problems associated with the fractional separation of an etherification reaction zone product stream. Specifically, the presence of alcohol in an etherification reaction zone product stream often causes difficulty in separation of the ether product due to the azeotropic compositions formed with the hydrocarbons and ethers of the etherification reaction zone product stream. The amount of alcohol contained in the etherification reaction zone product stream is generally set by the concentration of isobutylene contained in the etherification reaction zone feed. As the concentration of isobutylene increases, the stoichiometric requirement of alcohol reactant correspondingly increases. Therefore, as the alcohol concentration in the etherification reaction zone feed increases, there is also a corresponding increase in the amount of alcohol contained in the etherification reaction zone product stream.

The etherification reaction zone product stream is charged or fed to a fractionation column which defines a separation zone and provides for the separation of such etherification reaction zone product stream, or reaction product, into an overhead product containing a non-reactive and/or unreacted hydrocarbons and a bottoms product containing the ether product.

In a typical etherification process operation, it is more desirable to produce a fractionator bottoms product comprising ether that is substantially free of alcohol. Thus, in conventional ether processes, the fractionator overhead product preferably contains most of the alcohol contained in the etherification reaction zone product stream. However, in the instant invention, an ETBE reaction product is produced within an etherification reaction zone, and it is desired for the unreacted ethanol reactant to pass with the fractionator bottoms product along with the ETBE reaction product instead of as a part of the fractionator overhead product.

A key problem with performing a fractional separation between the non-reactive hydrocarbons and ethanol of the etherification reaction zone product stream is the formation of azeotropes, also known as constant boiling mixtures, which prevent a satisfactory separation of the two components. This inability to perform an adequate separation of the hydrocarbons and ethanol by fractional distillation can result in a significant loss of ethanol in the fractionator overhead product when it is desired to recover the ethanol with the ether of the fractionator bottoms product.

The presence of ethanol in the fractionator overhead product has two disadvantages. One disadvantage is associated with the difficulty in effectively removing ethanol from the fractionator overhead product prior to passing the resultant ethanol-free hydrocarbons to downstream processing units such as HF alkylation. A small amount of ethanol in the feed of some of the downstream processing units can have an enormous detrimental impact on such units. Another disadvantage to the presence of large quantities of ethanol in the fractionator overhead product is simply the undesirable lack of recovery of ethanol as a fractionator bottoms product.

In order to improve the amount of ethanol recovered along with the ETBE of the fractionator bottoms product, it has been discovered that methanol can be provided or added to the etherification reaction zone product stream to give a fractionator feed having a concentration of methanol relative to the ethanol content of the fractionator feed within certain critical ranges. Without wanting to be bound by any particular theory, it is believed that the utilization of methanol as an additive to the fractionator feed to enhance the recovery of ethanol in the fractionator bottoms product works by interfering with the formation of azeotropes of ethanol and hydrocarbons. This interference with the azeotropic compositions allows for the recovery of a fractionator overhead product that is substantially free of ethanol but containing methanol and hydrocarbons and a fractionator bottoms product containing ETBE and ethanol.

For the inventive process, it is generally desirable to use a quantity of methanol with the fractionator feed that is effective in providing a substantially ethanol free fractionator overhead product. Thus, the amount of methanol utilized is such as to allow for the fractional separation of the fractionator feed into a fractionator overhead product generally containing less than about 1.5 mol percent ethanol but, preferably, less than about 1.0 mol percent ethanol and, most preferably, less than 0.5 mol percent ethanol.

The quantity of methanol provided in the fractionator feed is set by the desired percent recovery of the ethanol contained therein by way of the fractionator bottoms product. The molar ratio of methanol to ethanol in the fractionator feed is the critical ratio which impacts the percent recovery of ethanol; and, generally, it can be in the range of from about 0.1:1 to about 10:1. For more optimum recovery of the ethanol in the fractionator bottoms product, however, the molar ratio of methanol to ethanol can be in the range of from about 0.25:1 to about 7.5:1. Preferably, the molar ratio of methanol to ethanol in the fractionator feed is in the range of from about 0.5:1 to about 5:1 and, most preferably, from 1:1 to 3:1.

The molar ratio of methanol to ethanol in the fractionator feed is a critical aspect of this invention and determines the percent ethanol that is recovered along with the ETBE in the fractionator bottoms product. Generally, at least about 70 weight percent of the ethanol in the etherification reaction zone product stream should pass with the fractionator bottoms stream. It is preferred, however, that at least about 80 weight percent of the ethanol in the etherification reaction zone product stream be recovered in the fractionator bottoms product and, most preferably, at least 95 weight percent of the ethanol is to be recovered.

The etherification reaction zone product stream is produced by charging an etherification reaction zone feedstream containing ethanol, etherifiable olefins such as iso-olefins, and other non-reactive hydrocarbons to an etherification reaction zone wherein the iso-olefins present in the feedstream are converted to ethers by reaction with primary or secondary alcohols in the presence of an acid ion exchange resin catalyst. Generally, the iso-olefins include those hydrocarbons having 5 to 16 carbon atoms per molecule. Examples of such iso-olefins include isobutylene, isoamylene, isohexylene, isoheptylene, isooctylene, isononylene, iosdecylene, isoundecylene, isododecylene, isotridecylene, isotetradecylene, isopentadecylene, and isohexadecylene, or mixtures of two or more thereof.

The alcohols which may be utilized as an etherification reactant include the primary and secondary aliphatic alcohols having from 1 to 12 carbon atoms, such as methanol, ethanol, propanol, isopropanol, the primary and secondary butanols, pentanols, hexanols, ethylene glycol, propylene glycol, butylene glycol, the polyglycols and glycerol, etc., or mixtures of two or more thereof.

The presently preferred reactants to the etherification reaction zone are ethanol and isobutylene because they yield ethyl tertiary butyl ether (ETBE) which has utility as an octane improver for gasoline. The ethanol also has utility as an octane improving blending component for gasoline. Accordingly, it is currently preferred for the iso-olefins to be predominately isobutylene and the alcohol predominately ethanol.

In a typical etherification process, the iso-olefin and the alcohol feedstream is passed through the etherification reaction zone in the presence of diluents which do not have an adverse effect upon the etherification reaction. The diluents can be present in a separate stream, but usually the diluent is in the iso-olefin stream. Examples of typical diluents include non-reactive hydrocarbons such as alkanes and straight chain olefins. The feed to the etherification reaction zone, excluding alcohol, is generally diluted so as to include about 2 to about 80 weight percent non-reactive hydrocarbons and olefins, preferably from about 10 to about 60 weight percent and, more preferably, from 30 to 50 weight percent.

The acid ion-exchange catalysts useful in the etherification reaction zone of the present invention are relatively high molecular weight carbonaceous material containing at least one $SO_3H$ functional group. These catalysts are exemplified by the sulfonated coals ("Zeo-Karb H", "Nalcite X" and "Nalcite AX") produced by the treatment of bituminous coals and sulfuric acid and commercially marketed as zeolitic water softeners or base exchangers. These materials are usually available in a neutralized form and in this case must be activated to the hydrogen form by treatment with a strong mineral acid such as hydrochloric acid and water washed to remove sodium and chloride ions prior to use. The sulfonated resin type catalysts are preferred for use in the present invention. These catalysts include the reaction products of phenol formaldehyde resins with sulfuric acid ("Amberlite IR-1", "Amberlite IR-100" and "Nalcite MX"). Also useful are the sulfonated resinous polymers of coumarone-indene with cyclopentadiene, and furfural and sulfonated polymers of cyclopentadiene with furfural. The most preferred cationic exchange resins are strongly acidic exchange resins consisting essentially of sulfonated polystyrene resin, for instance, a divinylbenzene cross-linked polystyrene matrix having from 0.5 to 20 percent and preferably from 4 to 16 percent of copolymerized divinylbenzene therein to which are ionizable or functional nuclear sulfonic acid groups. These resins are manufactured and sold commercially under various grade names such as "Dowex 50", "Nalcite HCR" and "Amberlyst 15". As commercially obtained they have solvent contents of about 50 percent and can be used as is or the solvent can be removed first. The resin particle size is not particularly critical and therefore is chosen in accordance with the manipulative advantages associated with any particular size. Generally mesh sizes of 10 to 50 U.S. Sieve Series are preferred. The reaction may be carried out in either a stirred slurry reactor or in a fixed bed continuous flow reactor. The catalyst concentration in a stirred slurry reactor should be sufficient to provide the desired catalytic effect. Generally catalyst concentration should be 0.5 to 50 percent (dry basis) by weight of the reactor contents with from 1 to 25 percent being the preferred range.

Acid ion exchange resins, such as Rohm & Haas Amberlyst 15 and Dow Chemical Dowex M-31, are currently the most preferred catalysts for the etherification.

The temperature for the etherification reaction zone and the space velocity for the feed to the etherification reaction zone can be selected as desired depending upon the degree of conversion desired and the temperature at which oligomerization becomes a problem. Generally, the temperature of the etherification reaction zones will be in the range of about 86° F. to about 248° F., preferably about 95° F. to about 176° F. Pressures are generally selected to ensure that the charges and the products remain in the liquid phase during the reaction. Typical pressures are in the range of about 30 to about 300 psig. Generally, the liquid hourly space velocity (LHSV) of feed in the reactor will be in the range of about 1 to about 10 $hr^{-1}$, preferably from about 2 to about 8 $hr^{-1}$, and most preferably from 3 to 6 $hr^{-1}$.

The molar ratio of alcohol to iso-olefin in the etherification reaction zone feed will generally be in the range of about 0.5:1 to about 4:1, preferably from about 0.8:1 to about 1.2:1, and most preferably about 1:1.

The etherification reaction zone product stream containing ether, alcohol and hydrocarbon is charged or passed to the fractionation column, as previously described, which provides separation means for separating the etherification reaction zone product stream into a fractionator overhead product and a fractionator bottoms product. The separation means is preferably a conventional distillation unit which includes a distillation column or fractionator equipped with trays or with packing for providing liquid-vapor contact. A general description of distillation operations is provided in *perry's Chemical Engineers' Handbook, Sixth Edition*, published by McGraw-Hill, Inc., 1984 at pages 13–5, through 13–9, which text is incorporated herein by reference.

As described earlier herein, mixed with the etherification reaction zone product stream is a controlled amount of methanol such as to permit the reduction in the ethanol concentration in the fractionator overhead product thereby providing for a high recovery of the unreacted ethanol. The fractionator overhead product passes to a downstream separation system for separating the methanol from the hydrocarbons.

Any conventional or nonconventional separation system can be employed to separate the methanol from the hydrocarbon of the fractionator overhead product provided it gives a separated hydrocarbon stream having less than about 1.0 mole percent methanol, preferably, less than about 0.5 mole percent and, most preferably, less than 0.20 mole percent. The preferred separation system includes a contacting means for contacting a water stream containing water with the fractionator overhead product and to provide the separated hydrocarbon stream, or a methanol lean raffinate stream, and a methanol rich extract stream. The water stream serves as a solvent.

The methanol rich extract stream passes to a fractionator which separates the methanol and water. The separated water can serve as the water stream, and the separated methanol can serve as a methanol stream by recycling and, therefore, mixing it with the etherification reaction product stream prior to charging the resultant mixture as the fractionator feed to the etherification reaction zone product fractionator.

Now referring to FIG. 1, there is provided a schematic representation of process system 10 that includes etherification reactors 12*a* and 12*b*, which are placed in series, etherification reaction zone product fractionator 14, and separation system 16. The separation system 16 further includes contactor 18 and fractionator 20.

An etherification reaction zone feed stream containing isobutylene, ethanol, and other non-reactive hydrocarbons is charged to etherification reactors 12*a* and 12*b* by way of conduit 22. The etherification reactors 12*a* and 12*b* define etherification reaction zones. Contained within these etherification reactors 12*a* and 12*b* is a suitable etherification catalyst, and the etherification reactors 12*a* and 12*b* are operated under suitable etherification reaction conditions in order to produce a reaction product containing ETBE, unreacted ethanol, and non-reactive hydrocarbons. The reaction product passes by way of conduit 24 to etherification reaction zone product fractionator 14. A methanol stream is introduced into the reaction product by way of conduit 26 and the thus-mixed fractionator feed is charged to etherification reaction zone product fractionator 14 by way of conduit 28.

The etherification reaction zone product fractionator 14 defines a separation zone and provides means for separating the fractionator feed into a fractionator overhead stream, primarily containing methanol and non-reactive hydrocarbons, and a fractionator bottoms stream, primarily containing ETBE and ethanol. The fractionator bottoms stream passes through conduit 30 downstream to either storage or further processing.

The fractionator overhead stream passes from etherification reaction zone product fractionator 14 by way of conduit 32 to separation system 16, which defines a separation zone and provides means for separating the fractionator overhead stream into a methanol stream containing methanol and a methanol lean raffinate stream containing non-reactive hydrocarbons. More specifically, the fractionator overhead stream passes through conduit 32 to contactor 18, which defines a contacting zone and provides means for contacting the fractionator overhead stream with a water extractant passing from contactor 18 by way of conduit 34 is the methanol lean raffinate stream. An extract rich in methanol passes through conduit 36 to fractionator 20, which defines a separation zone and provides means for separating the extract into a water stream containing water and a methanol stream containing methanol. The water stream passes from fractionator 20 through conduit 38 to contactor 18 to be used as the extractant. The methanol stream passes from fractionator 20 through conduit 40 and then to conduit 26, through which it is introduced into the etherification reaction zone product stream passing through conduit 24 with the resultant mixture passing to etherification reaction zone product fractionator 14 through conduit 28. Makeup methanol can be added to the process system 10 on an as needed basis by way of conduit 42.

The following calculated examples are presented to further illustrate the invention.

EXAMPLE I

Presented in Table I are material balances from a process simulation of an etherification reaction zone product fractionator for a base case and an inventive case. The base case is the fractional separation of an etherification reaction zone product stream containing ethanol, ethers (primarily ethyl tertiary butyl ether) and hydrocarbons, but not containing methanol, into an overhead product and a bottoms product. The inventive case is the fractional separation of the same feed as used in the base case with the exception of the addition of methanol to the feed to give a molar ratio of methanol to ethanol in the feed of about 3:1.

TABLE I

Calculated Material Balance For an Etherification Reaction Zone Product Fractionator for a Comparative Case Which Utilizes No Methanol in the Feed and an Inventive Case Which Utilizes a Molor Ratio of Methanol to Ethanol in the Fractionator Feed of 3:1

| | Fractionator Feed | | Overhead Product | | Bottoms Product | |
|---|---|---|---|---|---|---|
| Stream Name* | Base | Inventive | Base | Inventive | Base | Inventive |
| Temp [F.] | 112.30 | 112.30 | 100.28 | 101.37 | 207.48 | 210.09 |
| Pres [psia] | 75.00 | 75.00 | 75.00 | 75.00 | 90.00 | 90.00 |
| Vapor Frac | 0.38 | 0.43 | 0.00 | 0.00 | 0.00 | 0.00 |
| Enth [MMBtu/h] | −45.78 | −48.76 | −37.74 | −40.43 | −9.95 | −10.66 |
| Total Flow [lbmol/h] | 680.09 | 713.69 | 595.10 | 624.69 | 84.99 | 89.00 |
| Propylene | 0.28 | 0.28 | 0.28 | 0.28 | 0.00 | 0.00 |
| Propane | 1.78 | 1.78 | 1.78 | 1.78 | 0.00 | 0.00 |
| I-Butene | 7.14 | 7.14 | 6.90 | 6.97 | 0.24 | 0.16 |
| I-Butane | 552.09 | 551.09 | 543.24 | 545.67 | 7.85 | 5.42 |
| N-Butane | 23.80 | 23.80 | 16.62 | 17.95 | 7.18 | 5.85 |
| 1-Butene | 8.48 | 8.48 | 8.18 | 8.27 | 0.30 | 0.21 |
| Trans-2-Butene | 10.81 | 10.81 | 7.10 | 7.74 | 3.70 | 3.07 |
| Cis-2-Butene | 7.43 | 7.43 | 3.29 | 3.71 | 4.14 | 3.72 |
| 1,3-Butadiene | 0.99 | 0.99 | 0.99 | 0.99 | 0.00 | 0.00 |
| I-Pentane | 0.93 | 0.93 | 0.00 | 0.00 | 0.93 | 0.93 |
| N-Pentane | 0.00 | 0.00 | 0.00 | 0.00 | 0.00 | 0.00 |
| N-Hexane | 0.07 | 0.07 | 0.00 | 0.00 | 0.07 | 0.07 |
| Diethyl Ether | 0.30 | 0.30 | 0.00 | 0.00 | 0.30 | 0.03 |
| Ethanol | 11.23 | 11.23 | 3.75 | 0.23 | 7.48 | 11.00 |
| Tert-Butanol | 2.03 | 2.03 | 0.00 | 0.00 | 2.03 | 2.03 |
| 1-Diisobutylene | 0.01 | 0.01 | 0.00 | 0.00 | 0.01 | 0.01 |
| T-But EthylEther | 50.75 | 50.75 | 0.00 | 0.00 | 50.75 | 50.75 |
| Water | 2.97 | 2.97 | 2.97 | 2.68 | 0.00 | 0.29 |
| Methanol | 0.00 | 33.60 | 0.00 | 28.43 | 0.00 | 5.17 |

*Component flows are in lbmol per hour.

As can be seen from the information presented in Table I, the addition of methanol to the fractionator feed enhances the recovery of ethanol in the bottoms product. In the base case, 3.75 lb. moles per hour of ethanol passes with the overhead product. In the inventive case, on the other hand, less than 0.25 lb. moles per hour of ethanol passes with the overhead product. This difference illustrates the improvement in ethanol recovery with the fractionator bottoms product that results from the utilization of a methanol additive in the etherification reaction zone product stream.

EXAMPLE II

Figure 2:
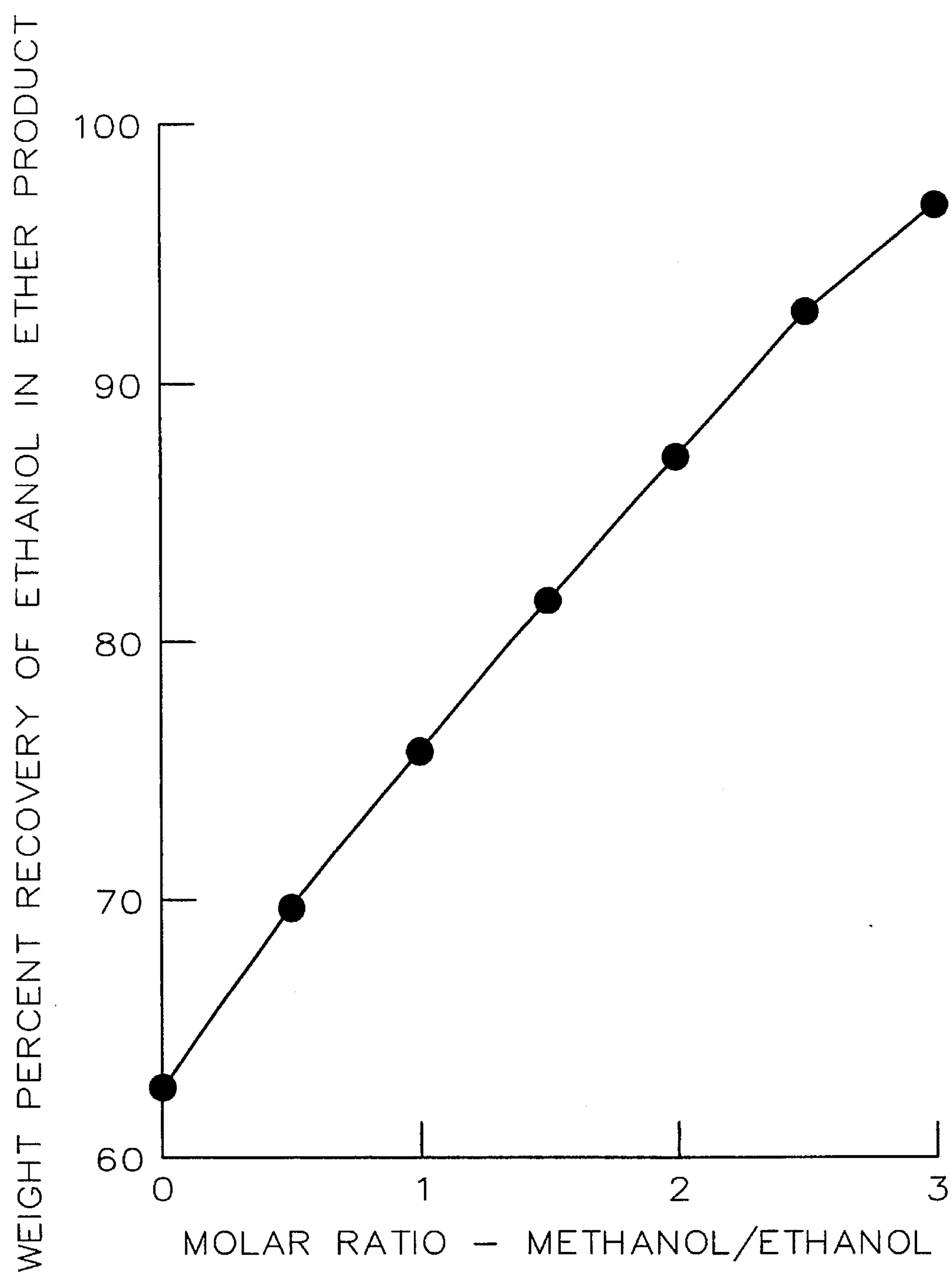
FIG. 2 is a plot which shows the weight percent recovery of ethanol in an ether fractionator bottoms product as a function of the molar ratio of methanol to ethanol in the ether fractionator feed.

This Example presents ethanol recovery data showing the improvement in the weight percent recovery of ethanol from an etherification reaction zone product stream through the use of methanol as an additive to such stream prior to fractionation. The data presented in Table II was generated using a standard fractionation simulation package while utilizing phillips petroleum Company proprietary vapor-liquid equilibrium thermodynamic physical property data. The data of Table II are plotted in FIG. 2. It is also demonstrated that the weight percent ethanol recovery improves as the molar ratio of methanol to ethanol increases.

TABLE II

Ethanol Recovery From an Etherification Reaction Zone Product as a Function of the Methanol-to-Ethanol Molar Ratio

| Molar Ratio (Methanol/Ethanol) | Ethanol Recovered in ETBE Bottoms Product (Weight Percent) |
|---|---|
| 0 | 62.7 |
| 0.5 | 69.7 |
| 1.0 | 75.7 |
| 1.5 | 81.7 |
| 2.0 | 87.3 |
| 2.5 | 92.9 |
| 3.0 | 96.9 |

That which is claimed is:

1. A method for producing ethyl tertiary butyl ether (ETBE), said method comprises the steps of:

reacting a stream containing isobutylene, ethanol and non-reactive reactive hydrocarbons within an etherification reaction zone to form a reaction product containing ETBE, ethanol, and non-reactive hydrocarbons;

adding a methanol stream containing methanol to said reaction product to give a fractionator feed such that the molar ratio of methanol to ethanol in said feed is in the range of from about 0.1:1 to about 10:1; and separating by fractionation said feed into an overhead stream and a bottoms stream, said overhead stream containing methanol and non-reactive hydrocarbons and said bottoms stream containing ETBE and ethanol.

2. A method as recited in claim 1, further comprising:

contacting said overhead stream with a water stream containing water within an extraction zone to thereby extract methanol from said overhead stream and providing a methanol lean raffinate stream containing non-reactive hydrocarbons and a methanol rich extract stream; and separating said methanol rich extract stream into said water stream and said methanol stream.

3. A method as recited in claim 1, wherein at last 70 weight percent of the ethanol in said reaction product is contained in said bottoms stream.

4. A method as recited in claim 3 whereto said reaction product has a concentration of methanol of less than 1 weight percent.

5. A method as recited in claim 4 wherein said overhead stream has a concentration of ethanol of less than 1 weight percent.

6. A method as recited in claim 5 whereto said methanol stream has a concentration of methanol exceeding 90 weight percent.

7. A method as recited in claim 2 wherein said methanol lean raffinate stream has a concentration of alcohol less than 1 weight percent.

8. A method as recited in claim 7 wherein said reaction product has a concentration of methanol of less than 1 weight percent.

9. A method as recited in claim 8 whereto said overhead stream has a concentration of ethanol of less than 1 weight percent.

10. A method as recited in claim 9 whereto said methanol stream has a concentration of methanol exceeding 90 weight percent.

11. A method for improving the recovery of ethanol contained in an etherification reaction zone product stream containing ethyl tertiary butyl ether (ETBE), ethanol and hydrocarbons, said method comprises the steps of:

providing a concentration of methanol in said etherification reaction zone product stream such that the molar ratio of methanol to ethanol is in the range of from 0.1:1 to about 10:1; and thereafter separating by fractionation said etherification reaction zone product stream into an overhead stream, containing methanol and hydrocarbons, and a bottoms stream containing ETBE and ethanol.

12. A method as recited in claim 11 wherein at least 70 weight percent of the ethanol in said etherification reaction zone product stream is contained in said bottoms stream.

13. A method as recited in claim 12 wherein said concentration of methanol provided in said etherification reaction zone product stream is such that the molar ratio of methanol to ethanol is in the range of from about 0.25:1 to about 7.5:1.

14. A method as recited in claim 13 wherein said etherification reaction zone product stream has a concentration of methanol less than 1 weight percent prior to providing said concentration of methanol.

15. A method as recited in claim 14 wherein said overhead product has a concentration of ethanol less than 1 weight percent.

16. A method as recited in claim 15 wherein at least 95 weight percent of the ethanol in said etherification reaction zone product stream is contained in said bottoms stream.

* * * * *

UNITED STATES PATENT AND TRADEMARK OFFICE
CERTIFICATE OF CORRECTION

PATENT NO. : 5,600,024

DATED : February 04, 1997

INVENTOR(S) : Robert B. Eldridge and Gary R. Patton

It is certified that error appears in the above-identified patent and that said Letters Patent is hereby corrected as shown below:

Column 9, claim 4, line 6, delete "whereto" and insert therefor --- wherein ---.

Column 9, claim 6, line 12, delete "whereto" and insert therefor --- wherein ---.

Column 9, claim 9, line 21, delete "whereto" and insert therefor --- wherein ---.

Column 9, claim 10, line 24, delete "whereto" and insert therefor --- wherein ---.

Signed and Sealed this

Twentieth Day of May, 1997

Attest:

BRUCE LEHMAN

*Attesting Officer* *Commissioner of Patents and Trademarks*